United States Patent
Garrett et al.

(10) Patent No.: US 9,511,062 B2
(45) Date of Patent: Dec. 6, 2016

(54) COMPACTED RUMEN PROTECTED NUTRIENT PELLETS AND METHOD OF MANUFACTURE

(75) Inventors: Jack Ellwyn Garrett, Longmont, CO (US); Greg Alan Nunnery, Round Rock, TX (US); Michael John Hodgens, Prior Lake, MN (US); Kyle Arthur Brokken, Eagen, MN (US)

(73) Assignee: Qualitech, Inc., Chaska, MN (US)

( * ) Notice: Subject to any disclaimer, the term of this patent is extended or adjusted under 35 U.S.C. 154(b) by 0 days.

(21) Appl. No.: 14/008,045

(22) PCT Filed: Mar. 22, 2012
(Under 37 CFR 1.47)

(86) PCT No.: PCT/US2012/030091
§ 371 (c)(1),
(2), (4) Date: May 9, 2014

(87) PCT Pub. No.: WO2012/134942
PCT Pub. Date: Oct. 4, 2012

(65) Prior Publication Data
US 2014/0294984 A1 Oct. 2, 2014

Related U.S. Application Data

(60) Provisional application No. 61/469,905, filed on Mar. 31, 2011.

(51) Int. Cl.
*A23K 1/00* (2006.01)
*A23K 1/14* (2006.01)
*A61K 31/455* (2006.01)
*A61K 9/16* (2006.01)

(52) U.S. Cl.
CPC ........... *A61K 31/455* (2013.01); *A23K 20/142* (2016.05); *A23K 20/158* (2016.05); *A23K 20/174* (2016.05); *A23K 20/22* (2016.05); *A23K 20/24* (2016.05); *A23K 20/30* (2016.05); *A23K 40/35* (2016.05); *A61K 9/1617* (2013.01); *A61K 9/1682* (2013.01)

(58) Field of Classification Search
None
See application file for complete search history.

(56) References Cited

U.S. PATENT DOCUMENTS

| | | |
|---|---|---|
| 4,087,556 A | 5/1978 | Harte |
| 4,876,097 A | 10/1989 | Autant et al. |
| 5,080,917 A | 1/1992 | Itoh et al. |
| 5,152,995 A | 10/1992 | Runkel et al. |
| 5,190,775 A | 3/1993 | Klose |
| 5,244,669 A | 9/1993 | Satoh et al. |
| 5,589,187 A | 12/1996 | Wentworth et al. |
| 5,807,594 A | 9/1998 | King et al. |
| 5,871,773 A | 2/1999 | Rode et al. |
| 5,874,102 A | 2/1999 | LaJoie et al. |
| 6,013,286 A | 1/2000 | Klose |
| 6,022,566 A | 2/2000 | Miller |
| 6,106,871 A | 8/2000 | Miller |
| 6,231,895 B1 | 5/2001 | Emanuele et al. |
| 6,242,013 B1 | 6/2001 | Luhman et al. |
| 6,306,427 B1 | 10/2001 | Annonier et al. |
| 6,391,454 B1 | 5/2002 | Mao et al. |
| 6,403,143 B1 | 6/2002 | Bevans et al. |
| 6,521,249 B2 | 2/2003 | Block et al. |
| 6,797,291 B2 | 9/2004 | Richardson |
| 6,818,235 B2 | 11/2004 | Block et al. |
| 7,939,117 B2 | 5/2011 | Zuccarello et al. |
| 2002/0127259 A1 | 9/2002 | Orthoefer |
| 2008/0008779 A1 | 1/2008 | Zuccarello et al. |
| 2009/0252833 A1 | 10/2009 | Roman et al. |
| 2009/0252837 A1 | 10/2009 | Hendel et al. |
| 2010/0203106 A1 | 8/2010 | MacGregor et al. |
| 2010/0272852 A1 * | 10/2010 | Wright et al. .................. 426/2 |

FOREIGN PATENT DOCUMENTS

| | | |
|---|---|---|
| EP | 0940088 A3 | 12/1999 |
| GB | 1561168 | 2/1980 |
| WO | 0189575 A1 | 11/2001 |
| WO | 03015764 A1 | 2/2003 |
| WO | 2004041166 A3 | 5/2004 |
| WO | 2007149818 A2 | 12/2007 |

OTHER PUBLICATIONS

Balchem, "The Sure Thing for Effective, Efficient Niacin Delivery". 2005 Balchem Encapsulated.
Balchem, "One Encapsulated Product. Two Valuable Benefits". 2009 Balchem Animal Nutrition & health.
Balchem, "Niashure Rumen Protected Niacin". 2005 Balchem Animal Nutrition & Health.
Balchem, "Niashure Usage and Formulation Guidelines". 2005 Balchem Animal Nutrition & Health.
Ajinomoto , "AjiPro-L", 2010 Ajinomoto Heartland, Inc.
Ajinomoto , "AjiPro-L", 2011 Ajinomoto Heartland, Inc.
Kemin, "col. 24", 2010 Kemin Industries, Inc.
http://www.americandairymen.com/articles/kemin-acquires-encapsulation-technology, "Darymen Kemin acquires encapsulation technology and expands ruminant portfolio", Jan. 6, 2010 Kemin Industries, Inc.
Kemin, "Product Specifications", 2010 Kemin Industries, Inc.
Kemin, "LYS-50", 2010 Kemin Industries, Inc.
Kemin, "Methioplus", 2010 Kemin Industries, Inc.

* cited by examiner

*Primary Examiner* — Jessica Worsham
(74) *Attorney, Agent, or Firm* — Sherrill Law Offices, PLLC

(57) ABSTRACT

A process for producing a compacted rumen-protected nutrient pellet and the resultant pellet. The process includes the steps of (i) blending a C4-24 fatty acid and a biologically active ingredient to form solid central core particles, (ii) compacting the core particles to form pellets, and (iii) sequentially coating the pellets with an organic solvent and a fatty acid alkali metal or alkaline earth metal salt.

37 Claims, No Drawings

COMPACTED RUMEN PROTECTED NUTRIENT PELLETS AND METHOD OF MANUFACTURE

BACKGROUND

Various nutrients fed to ruminants are degraded in the rumen, before they can reach the stomach and intestines where they are available for uptake. Many attempts have been made to protect nutrients from degradation in the rumen, such as those disclosed in U.S. Patent Application Publications 2008/008779, 2009/252833 and 2009/252837. While such attempts have generally been effective for increasing the percentage of nutrient surviving dwell time within the rumen, a continued need exists for improved rumen-protected nutrients.

SUMMARY OF THE INVENTION

A first aspect of the present claimed invention is a process for producing a compacted rumen-protected nutrient pellet. The process includes the steps of (i) blending a $C_{4-24}$ fatty acid and a biologically active ingredient to form solid central core particles, (ii) compacting the core particles to form pellets, and (iii) sequentially coating the pellets with an organic solvent and a fatty acid alkali metal or alkaline earth metal salt.

A second aspect of the present claimed invention is a compacted rumen-protected nutrient supplement comprising a compacted central core coated with sequentially applied coatings of an organic solvent and a fatty acid alkali metal or alkaline earth metal salt. The core includes at least a blend of a $C_{4-24}$ fatty acid and a biologically active ingredient.

DETAILED DESCRIPTION OF A PREFERRED EMBODIMENT

Definitions

As utilized herein, including the claims, the term "long chain fatty acid" means a fatty acid with an aliphatic tail longer than 12 carbons.

As utilized herein, including the claims, the phrase "volume based particle size" is the diameter of a sphere that has the same volume as a given particle.

Composition

The compacted rumen-protected nutrient supplement comprises a compacted central core and a coating.

The compacted central core includes at least a blend of a $C_{4-24}$ fatty acid and a biologically active ingredient. Other constituents may be included in the compacted core including specifically, but not exclusively, inorganic acid salts and clays.

For most applications, particularly lactating dairy cattle, long chain fatty acids, such as those found in vegetable oils, are preferred. One suitable source of long chain fatty acids is castor oil.

The biologically active ingredient can be an amino acid, a vitamin, trace element, protein, protein equivalent, medicament, enzyme, inorganic acidic salt, clay, etc.

Suitable amino acids include all of the known amino acids, with a particular interest in the essential amino acids of isoleucine, leucine, lysine, methionine, phenylalanine, threonine, tryptophan and valine.

Suitable vitamins include specifically, but not exclusively, vitamin A (retinol), vitamin $B_1$ (thiamine or thiamine HCl), vitamin $B_2$ (riboflavin), vitamin $B_3$ (niacin), vitamin $B_6$ (pyridoxine or pyridoxine HCl), vitamin $B_7$ (biotin), vitamin $B_9$ (folic acid), vitamin C (ascorbic acid), vitamin $B_{12}$ (cobalamins), vitamin D (calciferol), vitamin E (tocopherol), vitamin $K_1$ (phylloquinone) and the like.

Suitable trace elements include specifically, but not exclusively, cobalt, copper, iodine, iron, manganese, selenium, tin, vanadium, zinc and the like.

Suitable protein ingredients include specifically, but not exclusively, cottonseed meal, soy meal, canola meal, dehydrated alfalfa, fish meal, dried blood or meat meal, powdered eggs, and the like.

Suitable protein equivalents include specifically, but not exclusively, urea, biuret, ammonium phosphate, and the like.

Suitable medicaments include specifically, but not exclusively, chlorotetracycline, monensin, oxytetracycline, poloxalene, promazine hydrochloride, sulfamethazine and the like.

Suitable enzymes include specifically, but not exclusively, lipolytic proteins.

The core can comprise from 10 to 50 wt %, preferably 10 to 40 wt % and most preferably 10 to 30 wt % fatty acid, and from 50 to 90 wt %, preferably 60 to 90 wt % and most preferably 70 to 50 wt % biologically active ingredient.

The coating is comprised of sequentially applied layers of an organic solvent and a fatty acid alkali metal or alkaline earth metal salt. The core can be coated any number of times with sequential layers of an organic solvent and a fatty acid alkali metal or alkaline earth metal salt, but each additional coating layer after the second tends to provide sharply diminishing returns.

Suitable organic solvents include any ruminant food grade organic compound or mixture that is a liquid at or near room temperature. Suitable organic solvents include specifically, but not exclusively, petroleum oils such as mineral oil, and vegetable oils such as canola oil, olive oil, palm oil, soy oil etc. A preferred organic solvent is mineral oil, due to its low cost and excellent wetting of both the core and the fatty acid alkali metal or alkaline earth metal salt.

Suitable fatty acid alkali metal or alkaline earth metal salts include specifically, but not exclusively, sodium ($Na^+$), potassium ($K^{30}$), magnesium ($Mg^{2+}$) and calcium ($Ca^{2+}$) salts of a $C_{4-24}$ fatty acid, preferably a $C_{12-24}$ long chain fatty acid. A preferred fatty acid alkaline earth metal salt, due to its low cost and superior ability to protectively encapsulate the core within the rumen, is calcium stearate.

The weight ratio of organic solvent to fatty acid alkali metal or alkaline earth metal salt in each coating is between 1:1 to 1:9, preferably between 2:3 to 1:4 and most preferably between 2:3 to 1:4.

The weight ratio of core particles to coating is 1:1 to 20:1, preferably 1:1 to 10:1 and most preferably 2:1 to 10:1.

The pellets can be formed into substantially any desired general shape, including specifically but not exclusively, defined shapes such as cuboidal, rectangular parallelepiped, cylindrical, circular barrel, and spherical, and amorphous shapes. Cylindrical pellets are generally preferred for ease of manufacture and reasonably low ratio of surface area to volume.

The coated pellets can be sized as desired so long as they provide a reasonably low ratio of surface area to volume (i.e., flakes require a significantly greater amount of coating per unit weight than other shapes and expose a relatively large surface area to the harsh environment of the rumen), are not rejected as unpalatable by the ruminant, and can bypass chewing to arrive in the rumen and stomach uncrushed. Generally, an average volume based particle size of between 0.2 to 0.4 inches has been found to be suitable, with a preference for an average volume based particle size of between 0.2 to 0.4 inches. When generally shaped as a cylinder, the coated pellet preferably has a length of between 0.5 to 1 inch and a diameter of between 0.1 to 0.25 inches.

Method of Manufacture

The process for producing a compacted rumen-protected nutrient pellet includes the steps of (i) blending a $C_{4-24}$ fatty acid and a biologically active ingredient to form solid central core particles, (ii) compacting the core particles to form pellets, and (iii) sequentially coating the pellets with an organic solvent and a fatty acid alkali metal or alkaline earth metal salt.

The fatty acid and biologically active ingredient can be blended together to form core particles by any of the well know blending techniques. A wide variety of suitable mixers and blenders are available from a number of suppliers. One such manufacturer is Littleford Day, Inc. of Florence, Ky.

The core particles can be compacted by any of the well know compaction techniques. A wide variety of suitable compaction machines are available from a number of suppliers. For most applications a pellet mill is the desired compaction tool. One manufacturer of a suitable line of pellet mills is California Pellet Mill Co. (CPM) of Crawfordsville, Ind.

The compacted pellets can be sequentially coated with an organic solvent and a fatty acid alkali metal or alkaline earth metal salt by any of the well know coating techniques, including specifically, but not exclusively, fluidized bed coating, centrifugal fluidized bed coating, pan coating, etc. A wide variety of coating equipment is available from a number of suppliers. For most applications pan coating is the desired coating technique. One manufacturer of a suitable line of coating equipment is Continental Products Corp of Milwaukee, Wis.

Method of Use

The compacted rumen-protected nutrient supplement pellets may be fed to ruminants by simply incorporating the pellets into the daily fodder or total mixed ration fed to the animals.

The amount of compacted rumen-protected nutrient supplement fed to a ruminant depends upon the specific nutrient (e.g., niacin or lysine), the type of ruminant (e.g., dairy cow or deer), the current condition of the ruminant (e.g., early lactating, late stage lactating or post-lactating dairy cow) and the desired biological effect (e.g., treatment of a diagnosed deficiency or meeting a daily recommended intake for general health). Those of routine skill in the art are capable of establishing the necessary and desired quantity to be fed.

EXPERIMENTAL

Experiment 1

Manufacture of Rumen Protected Niacin

Into a fifty five gallon electrically heated sprayer equipped with a #6570 nozzle was placed 162 lbs of castor oil. The castor oil was melted and continuously circulated with air at a temperature of 250 to 260° F. until applied.

Into the mixing drum of a LITTLEFORD SKM-1200E mixer was placed 646 lbs of niacin. With the drum and choppers operated at 60 Hz, the melted castor oil was sprayed into the drum at a rate of approximately 19 lbs per minute to form solid particles. The solid particles were allowed to cool for one hour with periodic jogging of the mixer and hand removal of any adhered material. The cooled solid particles were removed from the mixing drum and placed into a tote.

The solid particles were fed from the tote into a CALIFORNIA pellet mill having a 1 inch thick die with 0.125 diameter orifices sans relief. The solid particles were cycled through the pellet mill until heated to approximately 140 to 150° F., and then extruded through the die at a cutter setting of 0.75 inches to form compressed pellets. The compressed pellets were allowed to cool below 120° F.

The cooled compressed pellets were screened with a Romx model 2A AC/SS gyratory screen with a ¼ inch top screen and a 2M bottom screen.

800 lbs of the screened pellets were placed into a CONTINENTAL ROLLO-MIXER Mark VII model 50-26-60s rotary drum batch mixer. With the mixer operated at 60 Hz, 10.75 lbs of mineral oil was sprayed at 40 psi through a veejet 2501 nozzle at rate of approximately 1.7 lbs per minute onto the pellets within the mixer.

After completing spray coating of the pellets, 28.5 lbs of calcium stearate was added to the spray coated pellets within the mixer under constant mixing at 60 Hz. The combination of spray coated pellets and calcium stearate was mixed for five minutes.

The steps of spray coating with mineral oil and mixing with calcium stearate were repeated using 10.75 lbs of mineral oil and 28.5 lbs of calcium stearate to form twice coated rumen protected niacin pellets.

Experiment 2

Rumen Stability of Rumen Protected Products

Cobalt marked rumen protected niacin (Co-RPNi) was produced in accordance with Experiment 1 by blending 10 wt % Co-EDTA based upon the total weight of the rumen protected niacin pellets—into the core particles. In similar fashion cobalt marked rumen protected lysine (Co-RPLy) and cobalt marked rumen protected ascorbic acid (Co-RPAA) were produced by replacing the niacin with lysine and ascorbic acid, respectively.

Four ruminally cannulated Jersey cows were fed a common total mixed ration composed of chopped Lucerne hay, maize stover, maize meal, soybean oilcake, hominy chop, molasses, urea, Megalac and a vitamin/mineral premix containing 18% CP, 31.7% NDF and 21.3% starch on a dry matter basis.

The experiment was a 4×4 Latin Square design with four 14-day periods. Cows were ruminally dosed on day 11 with Cr-EDTA and one of the three rumen protected products (RPP) described supra to deliver 2.4 g of Co and 2.4 g of Cr. Rumen fluid samples were collected before dosing, at 2 hour intervals through 25 hours, and then every 4 hours until 49 hours post-dosing. These samples were analyzed for Co, Cr and pH.

Rumen pH was unaffected by treatment and averaged 5.88, with diurnal variation between 5.65 and 6.40 Animal performance was not affected by treatment with average milk production of 24.6 L/day, milk fat of 4.18% and milk protein of 3.56%.

The stability of the RPP within the rumen was measured as the proportion of the area under the curve of rumen clearance of Co (in the RPP as Co-EDTA) relative to the clearance of the Cr (as free Cr-EDTA). The rumen stability of Co-RPNi was the highest (P=0.06) at 66.7% relative to Co-RPLy at 55.0%, but only tended (P=0.14) to differ from Co-RPAA at 58.7%.

Simultaneous in sacco incubations of the RPP showed that the appropriate incubation time to estimate the in vivo rumen stability was ≈24 hours.

Experiment 3

Rumen Protected Niacin—Response to Epi Challenge

Niacin may modulate lipolytic responses in adipose tissue but is highly degradable in the rumen so that oral administration leads to unknown quantities absorbed. We determined responses to epinephrine (Epi) challenge as affected by three levels of protected niacin (PN) or unprotected niacin (UN) in the diet or infused abomasally.

Six multiparous rumen-cannulated Holstein cows (BW=656 kg; 128±23 days in milk) were used in a completely randomized 6×6 Latin Square with an extra period to quantify carryover effects. Periods consisted of 7 days for adaptation followed by 7 days for measurements. Cows were fed according to NRC (2001) recommendations. Treatments were: CON (no niacin), INF (abomassal infusion of 12 g UN), N12 (12 g UN), BN3 (3 g PN), BN6 (6 g PN), and BN12 (12 g PN). Treatments N12, BN3, BN6, and BN12 were top-dressed on the Total Mixed Ration (TMR) twice daily. Treatment INF was divided in 5 equal portions and infused every 4 hours. Cows receiving treatments other than INF were infused with the same volume of water at the same times.

On day 12, cows received an i.v. infusion of Epi (1.4 μg/kg BW). Blood was sampled at −45, −30, −20, −10, and −5 min before Epi infusion and 2.5, 5, 10, 15, 20, 30, 45, 60, 90, and 120 rain after. Total area under the curve (AUC) responses of nonesterified Fatty Acids (NEFA) and glucose concentrations in plasma were calculated using the trapezoidal rule.

A quadratic effect existed among treatments BN3, BN6, and BN12 (P=0.01) for NEFA AUC. Time to peak NEFA concentration tended (P=0.08) to be greater for N12 (22.1±3.2 min) than for EN12 (14.8±3 min). For glucose, INF resulted in greater AUC than N12 (P=0.04) and BN12 tended to have greater AUC than N12 (P=0.07). Glucose AUC displayed a quadratic response among treatments BN3, BN6, and BN12 (P=0.03). Time to peak and peak concentration of glucose, as well as NEFA peak concentration, did not differ (P>0.1).

In conclusion, dietary PN unexpectedly resulted in greater lipid mobilization in response to Epi challenge compared with cows receiving equivalent dietary UN.

Experiment 4

Rumen Protected Niacin—Effect Upon Milk Production

Six multiparous rumen-cannulated Holstein cows (BW=656 kg) after peak lactation (128±23 days in milk) were assigned to 1 of 6 treatments in a completely randomized 6×6 Latin Square with an extra period to measure carry-over effects. Periods consisted of a 7-day (d 1-7) adaptation period followed by a 7-day (d 8-14) measurement period. Cows were fed according to NRC (2001) recommendations to meet or exceed requirements. Treatments were: CON (no niacin), INF (abomassal infusion of 12 g unprotected niacin (UN)), N12 (12 g UN), BN3 (3 g PN), BN6 (6 g PN), and BN12 (12 g PN). Treatments N12, BN3, BN6, and BN 12 were top-dressed on the Total Mixed Ration (TMR) twice daily. The daily dose of treatment INF was divided in 5 equal portions and infused during the day every 4 hours. Cows receiving treatments other than INF were infused with the same volume of water at the same time.

Milk yield tended (P=0.06) to be greater for N12 (37.1±2.3 kg) than for BN12 (33.4±2.3 kg). The dry matter intake (DMI) was lower (P−0.02) for BN12 (21.5±1 kg) than for N12 (24.3±1 kg). The linear effect among BN3, BN6, and BN12 was significant (P=0.04) for DMI. Feed efficiency (FE=energy-corrected milk/DMI) was greater (P=0.04) for BN12 (1.7±0.1) than for N12 (1.5±0.1). Furthermore, the linear effect among BN3, BN6, and BN12 was significant (P=0.03). The milk fat/protein ratio (F/P) was higher (P=0.03) for BN12 (1.28±0.09) than for N12 (1.15±0.09). The linear effect among BN3, BN6, and BN12 was significant (P<0.01).

In conclusion, cows receiving BN12 had higher HP and FE but lower milk yield than cows receiving the same amount of UN.

We claim:

1. A process for producing a compacted rumen-protected nutrient pellet comprising:
    (a) blending a $C_{4-24}$ fatty acid and a biologically active ingredient to form solid central core particles,
    (b) compacting said core particles to form pellets, and
    (c) sequentially coating said pellets with an organic solvent which is liquid at room temperature selected from the group consisting of mineral oil and vegetable oil, and then an alkali or alkaline earth metal salt of a fatty acid to form a compacted central core having an inner coating of an organic solvent which is liquid at room temperature and an outer coating of an alkali or alkaline earth metal salt of a fatty acid.

2. The process of claim 1 wherein the biologically active ingredient is blended with a mixture of long chain fatty acids.

3. The process of claim 2 wherein the mixture of long chain fatty acids is a vegetable oil.

4. The process of claim 3 wherein the vegetable oil is castor oil.

5. The process of claim 1 wherein the biologically active ingredient is niacin or lysine.

6. The process of claim 1 wherein the organic solvent is a petroleum product.

7. The process of claim 6 wherein the petroleum product is mineral oil.

8. The process of claim 1 wherein the alkali or alkaline earth metal salt of a fatty acid is a long chain fatty acid alkali metal or alkaline earth metal salt.

9. The process of claim 8 wherein the long chain fatty acid alkali metal or alkaline earth metal salt of a fatty acid is calcium stearate.

10. The process of claim 1 wherein the solid central core comprises 10 to 50 wt % fatty acid and 50 to 90 wt % biologically active ingredient.

11. The process of claim 1 wherein the pellets are sequentially coated at least twice with an organic solvent and an alkali or alkaline earth metal salt of a fatty acid.

12. The process of claim 1 wherein the weight ratio of organic solvent to fatty acid alkali metal or alkaline earth metal salt of a fatty acid is between 1:1 to 1:9.

13. The process of claim 9 wherein the weight ratio of organic solvent to alkali or alkaline earth metal salt of a fatty acid is between 2:3 to 1:4.

14. The process of claim 1 wherein the weight ratio of pelletized core particles to both coatings is 1:1 to 20:1.

15. The process of claim 1 wherein the weight ratio of pelletized core particles to both coatings is 1:1 to 10:1.

16. The process of claim 1 wherein the coated pellets have an average volume based particle size of between 0.2 to 0.4 inches.

17. The process of claim 1 wherein the coated pellets have a length of between 0.5 to 1 inch and a diameter of between 0.1 to 0.25 inches.

18. The process of claim 2 wherein the $C_4$-$C_{24}$ fatty acid is heated to between 230 and 280° F. prior to blending with the biologically active ingredient.

19. The process of claim 18 wherein the heated $C_{4-24}$ fatty acid is spray coated onto solid particles of the biologically active ingredient.

20. The process of claim 1 wherein the core particles are compacted in a pellet mill.

21. The process of claim 4 wherein the core particles are compacted in a pellet mill by thermally heating the particles to between 120 and 150° F. to soften the particles, and extruding the softened particles through a dye having openings smaller than 0.1 $in^2$.

22. The process of claim 1 wherein the pellets are screened prior to coating to remove undersized pellets.

23. The process of claim 1 wherein the organic solvent is spray coated onto the pellets and the solvent coated pellets are then tumbled with the alkali or alkaline earth metal salt of a fatty acid.

24. The process of claim 23 wherein the sequential steps of spray coating organic solvent onto the pellets and tumble coating the alkali or alkaline earth metal salt of a fatty acid onto the solvent coated pellets is repeated at least once.

25. A compacted rumen-protected nutrient supplement comprising a compacted central core having an inner coating of an organic solvent which is liquid at room temperature selected from the group consisting of mineral oil and vegetable oil and an outer coating of an alkali or alkaline earth metal salt of a fatty acid, wherein the core includes at least a blend of a $C_{4-24}$ fatty acid and a biologically active ingredient.

26. The supplement of claim 25 wherein the $C_{4-24}$ fatty acid is a mixture of long chain fatty acids.

27. The supplement of claim 25 wherein the biologically active ingredient is niacin or lysine.

28. The supplement of claim 25 wherein the organic solvent is mineral oil.

29. The supplement of claim 25 wherein the alkali or alkaline earth metal salt of a fatty acid is an alkali or alkaline earth metal salt of a long chain fatty acid.

30. The supplement of claim 29 wherein the alkali or alkaline earth metal salt of a long chain fatty acid is calcium stearate.

31. The supplement of claim 25 wherein the compacted central core comprises 10 to 50 wt % fatty acid and 50 to 90 wt % biologically active ingredient.

32. The supplement of claim 27 wherein the compacted central core comprises 10 to 30 wt % fatty acid and 70 to 90 wt % biologically active ingredient.

33. The supplement of claim 25 wherein the compacted central core is sequentially coated at least twice with an organic solvent and an alkali or alkaline earth metal salt of a fatty acid.

34. The supplement of claim 25 wherein the weight ratio of organic solvent to alkali or alkaline earth metal salt of a fatty acid is between 2:3 to 1:4.

35. The supplement of claim 32 wherein the weight ratio of compacted central core to both coatings is 2:1 to 10:1.

36. A supplement mass comprising a plurality of coated pellets, each comprising a coated compacted central core in accordance with claim 25, wherein the coated pellets have an average volume based particle size of between 0.1 to 0.6 inches.

37. The supplement of claim 25 wherein the coated compacted central core has a length of between 0.5 to 1 inch and a diameter of between 0.1 to 0.25 inches.

* * * * *